United States Patent
Tsujita

(10) Patent No.: US 9,514,564 B2
(45) Date of Patent: Dec. 6, 2016

(54) ULTRASONIC DIAGNOSTIC APPARATUS AND ULTRASONIC IMAGE DISPLAY METHOD

(75) Inventor: Takehiro Tsujita, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 593 days.

(21) Appl. No.: 13/879,062

(22) PCT Filed: Jul. 28, 2011

(86) PCT No.: PCT/JP2011/067187
§ 371 (c)(1),
(2), (4) Date: Apr. 12, 2013

(87) PCT Pub. No.: WO2012/056778
PCT Pub. Date: May 3, 2012

(65) Prior Publication Data
US 2013/0194267 A1    Aug. 1, 2013

(30) Foreign Application Priority Data

Oct. 28, 2010    (JP) .................................. 2010-242494

(51) Int. Cl.
*G06T 15/08*    (2011.01)
*A61B 8/08*    (2006.01)
(Continued)

(52) U.S. Cl.
CPC .................. *G06T 15/08* (2013.01); *A61B 8/14* (2013.01); *A61B 8/463* (2013.01); *A61B 8/485* (2013.01);
(Continued)

(58) Field of Classification Search
None
See application file for complete search history.

(56) References Cited

U.S. PATENT DOCUMENTS

| 6,480,732 B1 | 11/2002 | Tanaka et al. |
| 2008/0260227 A1 | 10/2008 | Hayashi et al. |

(Continued)

FOREIGN PATENT DOCUMENTS

| CN | 101351156 A | 1/2009 |
| JP | A-2008-259605 | 10/2008 |
| JP | A-2009-34521 | 2/2009 |

OTHER PUBLICATIONS

Office Action issued in Chinese Application No. 201180052552.1 dated Aug. 11, 2014.

(Continued)

Primary Examiner — Diana Hickey
(74) Attorney, Agent, or Firm — Oliff PLC

(57) ABSTRACT

For generating ultrasonic projection images in which various kind of ultrasonic projection images have been appropriately combined, the invention is provided with: a storage unit that stores tomographic image volume data and elastic image volume data; a volume rendering unit that generates tomographic projection images by volume rendering on the basis of the tomographic image volume data; a display device that displays the ultrasonic projection images generated by the volume rendering unit; and an operation unit for inputting commands to control the volume rendering unit. For one of the rendering spaces partitioned by a cutting plane set in the rendering space by a command input from the operation unit, the volume rendering unit renders voxels of tomographic image volume data corresponding to the voxels of elastic image volume data that have elasticity values satisfying a set threshold value, and generates and displays the tomographic projection image on the display device.

14 Claims, 12 Drawing Sheets

(51) Int. Cl.
*A61B 8/14* (2006.01)
*A61B 8/00* (2006.01)
*A61B 8/06* (2006.01)

(52) U.S. Cl.
CPC ................ *A61B 8/5246* (2013.01); *A61B 8/06* (2013.01); *A61B 8/466* (2013.01); *A61B 8/483* (2013.01); *A61B 8/488* (2013.01)

(56) References Cited

U.S. PATENT DOCUMENTS

2009/0036749 A1      2/2009  Freiburger et al.
2009/0124903 A1*    5/2009  Osaka ............................ 600/443
2009/0306504 A1*  12/2009  Arai et al. .................... 600/443

OTHER PUBLICATIONS

Sep. 13, 2011 International Search Report issued in International Patent Application No. PCT/JP2011/067187.

\* cited by examiner

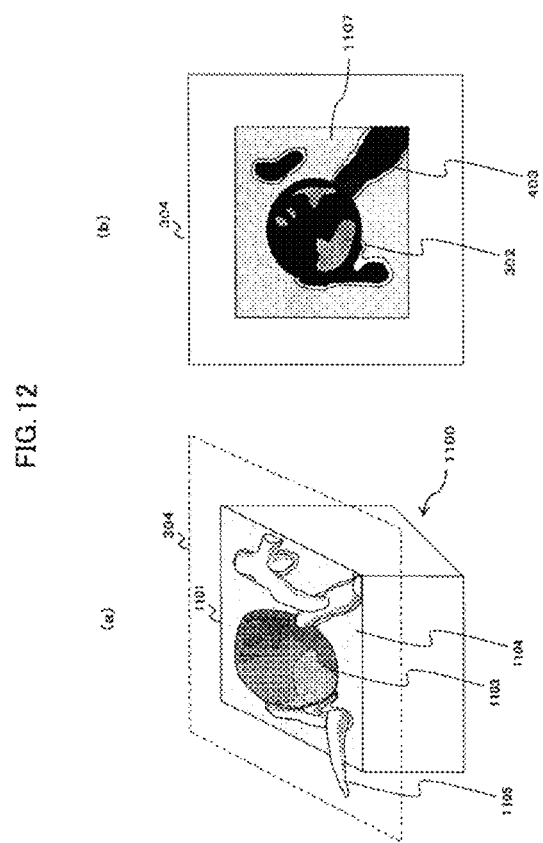

ULTRASONIC DIAGNOSTIC APPARATUS AND ULTRASONIC IMAGE DISPLAY METHOD

FIELD OF THE INVENTION

The present invention relates to an ultrasonic diagnostic apparatus, in particular to an ultrasonic diagnostic apparatus and an ultrasonic image display method capable of constructing and displaying a tomographic projection image on which another ultrasonic projection image such as an elasticity projection image is superimposed, utilizing a property of the ultrasonic projection image.

DESCRIPTION OF RELATED ART

An ultrasonic diagnostic apparatus transmits ultrasonic waves to an object to be examined from an ultrasonic probe, receives the reflected echoes of the ultrasonic waves returned from the biological tissue in the object by the ultrasonic probe, and generates RF frame data by performing a reception process such as phasing on the received reflected signals. On the basis of the generated RF frame data, a grayscale 2-dimensional tomographic image is generated and displayed on a display device. Another known configuration of an ultrasonic diagnostic apparatus is to generate tomographic volume data by obtaining plural pieces of 2-dimensional tomographic image data related to a certain block of biological tissue (volume), and to volume render the obtained data to construct and display a grayscale 3-dimensional tomographic projection image on a display device.

Similarly, another known configuration is to generate 2-dimensional elasticity frame data showing the hardness or softness of biological tissue in a diagnostic region based on two sets of RF frame data having different amount of compression applied to the biological tissue, so as to display an elasticity image which is colored in accordance with the elasticity values on the display device. Further, another known configuration is to generate elasticity image volume data by obtaining plural pieces of 2-dimensional elasticity frame data relating to the volume of biological tissue, then create by volume rendering a 3-dimensional elasticity projection image and display the image on the display device.

The purpose of displaying an elasticity projection image is to extract a hard tumor area surrounded by organs and observe the hardness of the tumor area or the condition of the surrounding tissue, so as to avoid an invasive examination or to determine an appropriate treatment strategy by determining the degree of malignancy in the tumor area. However, the tissue which surrounds a tumor area is generally solid, thus the tumor is hidden from a point of sight by the high luminance in the surrounding tissue and it is difficult to display both the tumor and the surrounding tissue at the same time using the method of generating and displaying a 3-dimensional elasticity projection image by a normal rendering process.

Considering this problem, Patent Document 1 proposes a technique, at the time of volume rendering a 3-dimensional tomographic projection image, for generating and displaying a tomographic projection image in which a hard area is enhanced by using an opacity table corresponding to the elasticity values in place of a generally used opacity table corresponding to the luminance values.

On the other hand, Patent Document 2 proposes a technique for displaying a tomographic image in an arbitrary cross-section set in a 3-dimensional tomographic projection image and a 3-dimensional blood flow projection image for visualizing the stereoscopic relationship between the tumor area and the blood flow, so that the existence of a feeding vessel penetrating into tumor tissue can be easily discriminated.

PRIOR ART DOCUMENTS

Patent Documents

Patent Document 1: JP-2008-259605
Patent Document 2: U.S. Patent No. 2006/480732

SUMMARY OF INVENTION

Technical Problem

However, for example the surrounding tissue of a target hard area cannot be clearly displayed on a tomographic projection image by the method disclosed in Patent Document 1, which makes it difficult to evaluate the degree of malignancy by comparing with the surrounding tissue. Also, the method disclosed in Patent Document 2 merely combines and displays a 2-dimensional tomographic image and a blood flow projection image, without considering the combination with other ultrasonic images which can optimize the characteristics thereof.

That is, with the progress of the ultrasonic diagnostic technique, broadening of potential in ultrasonic diagnosis is expected by constructing a tomographic projection image combined with various ultrasonic projection images using the characteristics thereof. However, construction of tomographic projection images using the characteristics of various ultrasonic images is not considered in the conversional techniques.

The objective of the present invention is to contribute to ultrasonic diagnosis by providing a technique capable of generating a tomographic projection image combined with other ultrasonic images such as an elasticity projection image.

BRIEF SUMMARY OF THE INVENTION

In order to solve the above-described problem, the present invention comprises:
a volume rendering unit configured to generate a tomographic projection image and an elasticity projection image by volume rendering based on the tomographic volume data and elasticity image volume data of the ultrasonic waves; and
a display device configured to display the tomographic projection image and the elasticity projection image generated by the volume rendering unit,
wherein the volume rendering unit, for one of the rendering spaces partitioned by a cutting plane set in the rendering space, renders the voxels in the tomographic image volume data corresponding to the voxels of the elasticity image volume data having the elasticity values that satisfy a set threshold value, generates and displays the tomographic projection image on the display device. The present invention also comprises:
a memory unit configured to store tomographic image volume data and elasticity image volume data; and
an operation unit configured to set a cutting plane to be set in a rendering space.
In this case, for the other one of the volume rendering spaces partitioned by the cutting plane, the volume rendering unit is capable of rendering the tomographic volume data to generate and display the tomographic projection image on the display device.

Here, the cutting plane can be set at least on one cross-section in the orthogonal three cross-sections displayed on the display device using tomographic volume data. In this case, the cutting plane can be set from the operation unit by moving a pointer displayed on a screen. Also, it is needless to say that the cutting plane is not limited to a flat surface, and may foe a curved surface or a winding surface.

In this manner, in accordance with the volume rendering unit of the present invention, when a tomographic projection image is observed by orthogonal 3-cross-sectional images, etc. on which a hard area exists though not shown being hidden inside the surrounding tissue, an examiner sets the hard area as a region of interest and also sets a cutting plane so that the set region of interest comes on the viewpoint side of the cutting plane. By doing so, the viewpoint side of the cutting plane is set as the region of which the tomographic projection image obtained by a normal rendering process is not displayed (non-display region), and a tomographic projection image of the biological tissue having the elasticity value that surpasses a threshold value is generated. On the other hand, the region in the opposite side of the cutting plane is set as a target region of the tomographic projection image by a normal rendering process.

As a result, for example when an area hidden inside of the surrounding tissue is likely hard tissue such as a tumor, a tomographic projection image is generated in which the voxels in the tomographic image volume data corresponding to the voxels having the elasticity value that satisfies a threshold value are volume rendered. In this manner, a tomographic projection image is generated and displayed in which the information of an elasticity projection image is reflected, which makes it easier for an examiner to understand the steric structure of a region of interest and broadens the potential in ultrasonic diagnosis. For example, since the surrounding tissue of a target hard area can be displayed in a tomographic projection image, the degree of malignancy can be evaluated by comparison with the surrounding tissue.

For example, in order to observe a tumor surrounded by solid tissue, a cutting plane is set to penetrate through the position including the tumor, and the area other than the tomographic image having a predetermined hardness is set not to be displayed on the viewpoint-side of the cutting plane. In this manner, the area including the surrounding area in the back side of the cutting plane can be displayed corresponding to a tumor area, thus a 3-dimensional tomographic projection image of the tumor area and the tomographic projection image of the surrounding area can be observed at the same time, whereby broadening the potential of the diagnosis. In this case, it is preferable that the tomographic projection image to be displayed on one side of the cutting plane is provided with colors in accordance with the elasticity values. Also, the threshold value of the elasticity value can be variably set as the range having the upper limit and the lower limit. In this case, an image showing an elasticity color scale can be displayed by juxtaposing next to the tomographic projection image to be displayed on the display device, so as to display the upper limit and the lower limit, of the threshold value in the elasticity color scale. The upper limit and the lower limit of a threshold value can be set via the operation unit on the elasticity color scale displayed on the display device.

The tomographic projection image of the present invention is not limited to the above-described embodiment. For example, in the rendering space on the viewpoint side of a cutting plane, an elasticity projection image having the elasticity value greater than the threshold value can be volume rendered and generated. In the same rendering space, an elasticity projection image can be generated by rendering the voxels of the elasticity image volume data having the elasticity value which satisfies the threshold value, and the tomographic projection image can be generated by performing normal rendering on the tomographic image volume data. Then the elasticity projection image and the tomographic projection image generated by normal rendering can be superimposed and displayed on the display device. Also, a blood flow projection image generated by volume rendering the blood flow image volume data in a region on the viewpoint side of the cutting plane can be added on the previously mentioned tomographic projection images.

In this manner, by displaying a blood flow projection image, it is possible to intuitively understand that a feeding vessel is flowing into a tumor area.

Also, at least one of the tomographic cross-sectional image, elasticity cross-sectional image and blood vessel cross-sectional image in the cutting plane can be displayed on the cutting plane. Therefore, displaying the tomographic cross-sectional image of the luminance distribution on the cutting plane and applying colors only to a desired hardness area in accordance with the elasticity values can facilitate a further intuitive understanding.

Also, the number of cutting planes does not have to be limited to one, and it is possible to set plural pieces of cutting planes in parallel. In this case, the regions sandwiched by plural cutting planes can be set as the regions in which the tomographic projection images by normal rendering are to be displayed, and the region on the outside of the plural cutting planes can be set as the region for displaying a tomographic projection image on which the elasticity information, etc. is added. Further, plural pieces of cutting planes can be set by the respective cross-sectional images in the orthogonal three cross-sections to be displayed on the display device.

EFFECT OF THE INVENTION

In accordance with the present, invention, a tomographic image can foe generated in which a tomographic projection image and other ultrasonic projection images such as an elasticity projection image are combined. As a result, the potential of ultrasonic diagnosis can be broadened by observing the tomographic projection images representing the steric structure of areas such as a diagnostic region and the surrounding tissue and the characteristics of various ultrasonic images.

BRIEF DESCRIPTION OF THE DRAWINGS

FIG. 12 is a display example of a tomographic projection image and a cross-sectional image by Embodiment 2.

DETAILED DESCRIPTION OF THE INVENTION

The ultrasonic diagnostic apparatus comprising a function for constructing and displaying a tomographic projection image of the present invention will be described below referring to the attached diagrams.

Embodiment 1

Figure 1:
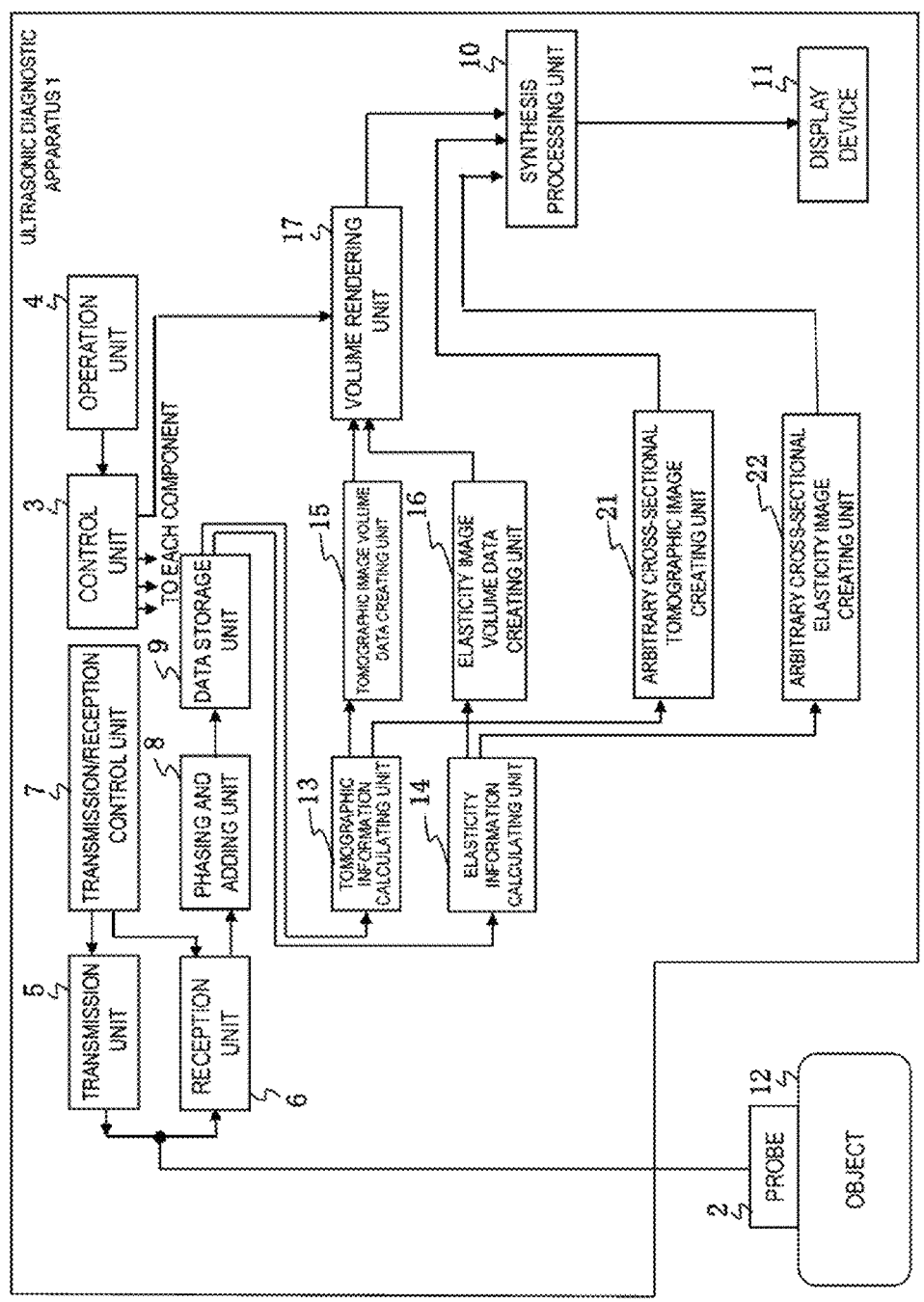
FIG. 1 is a block configuration diagram of an ultrasonic diagnostic apparatus in Embodiment 1 related to the present invention.

FIG. 1 shows a block configuration diagram of an ultrasonic diagnostic apparatus 1 in Embodiment 1 to which the present invention is applied. As shown in the diagram, the ultrasonic diagnostic apparatus 1 comprises an ultrasonic probe 2 to be used by applying on an object 12, a transmission unit 5 configured to repeatedly transmit ultrasonic waves to the object 12 at predetermined intervals via the ultrasonic probe 2, a reception unit 6 configured to receive the reflected echo signals reflected from the object 12, a transmission/reception control unit 7 configured to control the transmission unit 5 and the reception unit 6, and a phasing and adding unit 3 configured to perform phasing and adding of the reflected echoes received by the reception unit 6.

The ultrasonic probe is provided with plural transducers arrayed therein, and a function to transmit/receive ultrasonic waves to/from the object 12 via the transducers. The ultrasonic probe 2 is formed by plural transducers arrayed in a rectangular or fan shape, capable of 3-dimensionally transmitting/receiving ultrasonic waves by mechanically oscillating the transducers in the direction orthogonal to the array direction thereof. The ultrasonic probe 2 may also be provided with 2-dimensionally arrayed plural transducers for electronically controlling the transmission and reception of ultrasonic waves.

The transmission 5 generates transmission pulses for generating ultrasonic waves by driving the transducers of the ultrasonic probe 2. The transmission unit 5 has a function to set the convergent point of transmitted ultrasonic waves at a certain depth. The reception unit 6 generates the RF signal, i.e. reception signal by amplifying the reflected echo signal received by the ultrasonic probe 2 at a predetermined gain. The ultrasonic transmission/reception control unit 7 controls the transmission unit 5 and the reception unit 6.

The phasing and adding unit 8 control the phase of the RF signal amplified by the reception unit 6 and forms an ultrasonic beam with respect to one or more convergent points, so as to generate RF signal frame data (equivalent to RAW data). Further, in the ultrasonic diagnostic apparatus 1, the RF signal frame data generated in the phasing and adding unit 8 is stored in a data storage unit 9. A tomographic information calculating unit 13 constructs the tomographic frame data on the basis of the RF signal frame data stored in the data storage unit 9. A tomographic volume data creating unit 15 generates tomographic image volume data by performing 3-dimensional coordinate conversion based on the acquired position (coordinates) of the tomographic frame data constructed in the tomographic information calculating unit 13. A tomographic cross-sectional image creating unit 21 generates a tomographic cross-sectional image of an arbitrary position set via a device such as an operation unit 4 by inputting the tomographic frame data constituted in the tomographic information calculating unit 13.

The elasticity information calculating unit 14 constitutes 2-dimensional elasticity frame data on the basis of the plural sets of RF signal frame data stored in the data storage unit 9. The elasticity volume data creating unit 16 loads the elasticity frame data constituted in the elasticity information calculating unit 14 and performs 3-dimensional coordinate conversion on the basis of the acquired position (coordinates), so as to generate elasticity volume data. Also, the elasticity cross-sectional image creating unit 22 loads the elasticity frame data constituted in the elasticity information calculating unit 14, and generates an elasticity cross-sectional image of an arbitrary position set from a devise such as the operation unit 4. A volume rendering unit 17 generates a 3-dimensional tomographic projection image from the tomographic image volume data and a 3-dimensional elasticity projection image from the elasticity image volume data. Also, a synthesis processing unit 10 synthesizes an ultrasonic projection image generated by the volume rendering unit 17 with a tomographic cross-sectional image and an elasticity cross-sectional image generated by the tomographic cross-sectional image creating unit 21 and the elasticity cross-sectional image creating unit 22, on the basis of a display command set via a device such as the operation unit 4. The synthetic images created in the synthesis processing unit 10 or images such as 2-dimensional tomographic images or 2-dimensional elasticity images are displayed on the display device 11.

The ultrasonic diagnostic apparatus 1 also comprises a control unit 3 configured to control the above-described respective components and the operation unit 4 for inputting various commands to the control unit 3. The operation unit 4 comprises devices such as a keyboard or trackball.

Next, the detailed configuration and the operation of the main respective components will be described. The tomographic information calculating unit 13 performs signal processing such as gain compensation, log compression, detection, edge enhancement and filtering by inputting the RF signal frame data output, from the data storage unit 9 on the basis of the setting conditions set by the control unit 3, and constructs a 2-dimensional tomographic image.

The ultrasonic probe 2 is provided with plural transducers arrayed therein, for transmitting/receiving ultrasonic waves to/from the object 12 by electrically scanning beams. The ultrasonic probe 2 can instead be provided with plural transducers arrayed in a rectangular or fan-shaped form, for 3-dimensionally transmitting/receiving ultrasonic waves by mechanically oscillating the transducers in the direction orthogonal to the array direction thereof. The ultrasonic probe may also be formed by 2-dimensionally arrayed plural transducers for electronically controlling the transmission and reception of ultrasonic waves. That is, the ultrasonic probe 2 must be capable of measuring the reflected echo signals of the volume in a predetermined range of the object 12 while scanning beams by setting the scan plane of ultrasonic waves in the minor-axis direction, i.e. the direction orthogonal to the longitudinal array direction of the plural transducers. Also, the ultrasonic probe 2 must be capable of measuring scan angle θ of an ultrasonic beam in a scan plane and swing angle φ of an ultrasonic beam in the minor-axis direction. Then the ultrasonic probe 2 scans an ultrasonic beam on the scan plane by a transmitting/receiving unit while changing swing angle φ and receives the reflected echo signals from the object 12. The ultrasonic diagnostic apparatus 1 can measure the transmitting/receiving directions (φ, θ) at the same time as transmitting/receiving an ultrasonic wave.

The tomographic image volume data creating unit 15 performs 3-dimensional coordinate conversion on plural 2-dimensional tomographic images based on transmitting/receiving directions (φ, θ) which are equivalent to the acquired position of the 2-dimensional tomographic images, and generates the tomographic image volume data. To the tomographic image volume data, a color scale is provided in which the lightness changes in accordance mainly with the luminance such as a grayscale which varies from black to white or rubric sepia colored scale.

The elasticity information calculating unit 14 measures the displacement of biological tissue from plural sets of RF signal frame data stored in the data storage unit 9. Displacement of biological tissue can be applied by a known method or a mechanical compression, impact by ultrasonic waves or body motion such as beats, and is measured based on two pieces of RF signal frame data. Then the elasticity information calculating unit 14 calculates an elasticity value such as strain or elasticity modulus on the basis of the measured displacement, and creates 2-dimensional elasticity frame data. The elasticity image volume data creating unit 16 creates the elasticity image volume data by performing 3-dimensional coordinate conversion on plural sets of elasticity frame data based on the transmitting/receiving direction (φ, θ) equivalent to the acquired positions of the elasticity frame data, and generates the elasticity image volume data. A color value (blue, light blue, green, yellow, red, etc.) can be provided to the respective pixels of the elasticity image volume data in accordance with the elasticity.

The tomographic cross-sectional image creating unit 21 creates one or more 2-dimensional tomographic cross-sectional images relating to orthogonal three cross-sections from the tomographic image volume data created in the tomographic information calculating unit 13, on the basis of the command for specifying an arbitrary display cross-section to be set in the operation unit 4. In the same manner, the elasticity cross-sectional image creating unit 22 creates one or more 2-dimensional elasticity cross-sectional images relating to the orthogonal three cross-sections from the elasticity image volume data created in the elasticity information calculating unit 14 on the basis of the command for specifying an arbitrary display cross-section to be set in the operation unit 4. These tomographic cross-sectional images and elasticity cross-sectional images are superimposed in the synthesis processing unit 10 and displayed on the display device 11.

Since the characteristic of the present invention is in volume rendering, the characteristic configuration and operation of the volume rendering unit 17 in Embodiment 1 will be described in various examples.

Example 1

Figure 2:
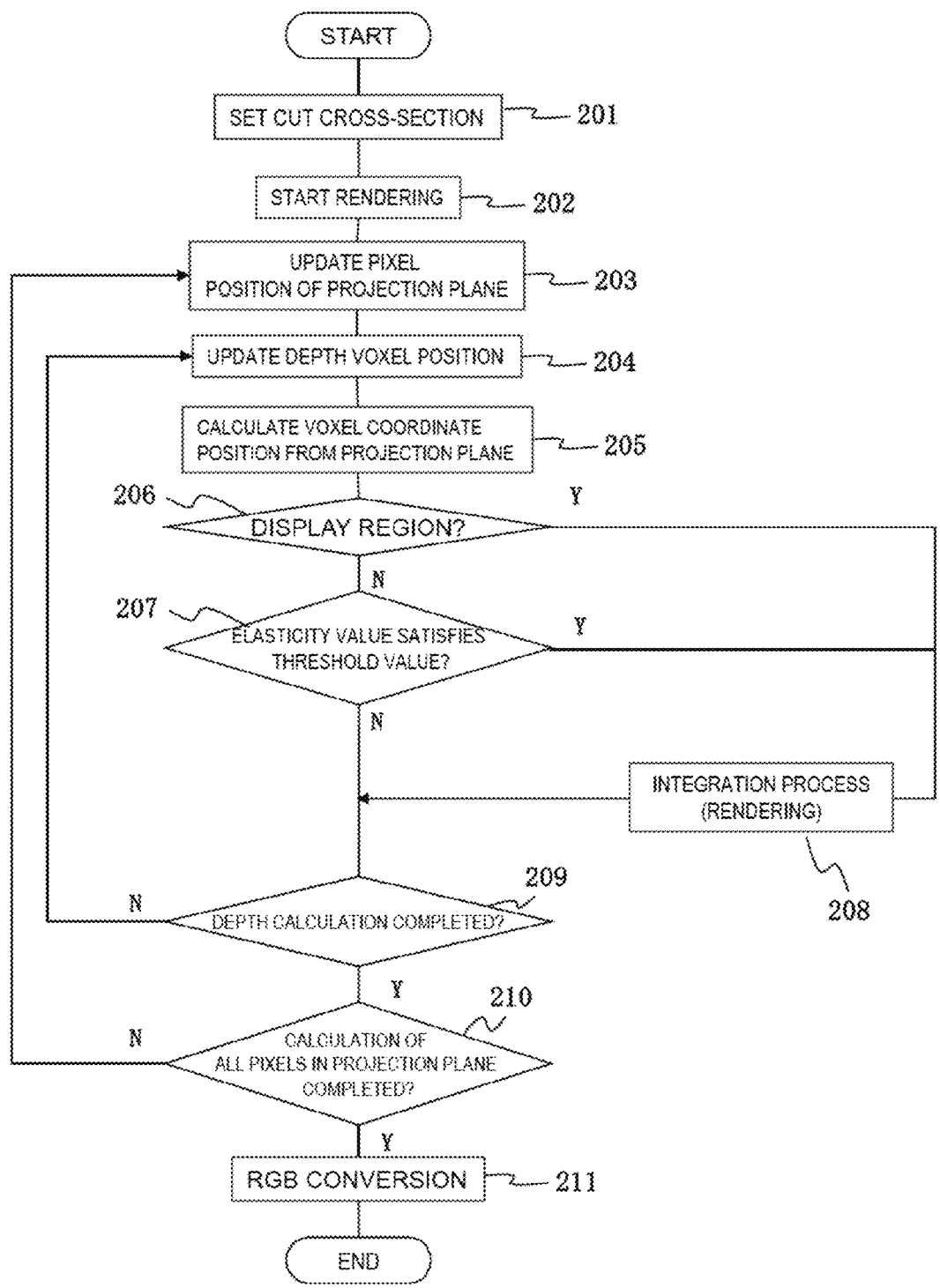
FIG. 2 is a flowchart showing the processing procedure of the volume rendering unit in Embodiment 1.
Figure 3:
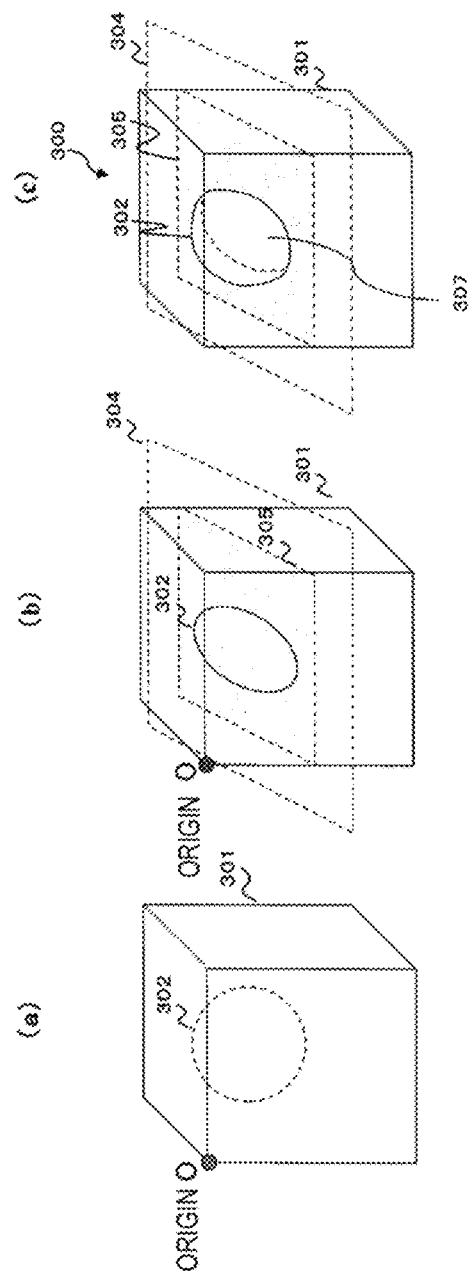
FIG. 3 is a pattern diagram for explaining the effect of a tomographic projection image by Embodiment 1.

FIG. 2 is a flowchart of the volume rendering unit 17 in Example 1, and FIG. 3 is a view for explaining the characteristic of an ultrasonic projection image generated by the present example. FIG. 3(a) is a pattern diagram showing a 3-dimensional tomographic projection image 301, which is an example that a hard tumor area 302 is contained inside of soft tissue. In this case, if a normal volume rendering is performed and the surrounding tissue of the tumor area 302 is soft tissue having a higher luminance than the tumor area 302, only the soft tissue hiding the tumor area 302 is depicted as the tomographic projection image 301, thus an examiner cannot identify the tumor area 302.

Here, as shown in the pattern diagram of FIG. 3(b), for example, a cutting plane 304 is set in tomographic volume data, and the viewpoint side of the cutting plane 304 (front side in the diagram) is set as a region in which the tomographic projection image 301 by normal volume rendering is not to be displayed (hereinafter arbitrarily referred to as a non-display region). Therefore, since the tomographic image by normal volume rendering is not displayed on the front side of the cutting plane 304, a cross-sectional image of the tumor area 302 is displayed on a cross-section 305 of the tomographic projection image 301 being cut by the cutting plane 304. In this manner, the examiner can identify that the tumor area 302 exists inside of the tomographic projection image 302. In the present example, an ultrasonic projection image 300 shown in FIG. 3(c) is to be further generated and displayed. That is, when the tomographic image volume data which is on the front side of the cutting plane 304 is volume rendered based on the hardness (elasticity value) of the biological tissue that is the characteristic of the tumor area 302 in order to obtain a projection image showing the form of the tumor area 302, for example a tomographic projection image 307 including a hemispherical tumor area 302 is displayed. In other words, the elasticity image volume data is detected, and the voxels which satisfy a threshold value are extracted while the elasticity value is variably set. Then the voxels of the tomographic image volume data corresponding to the extracted voxels are rendered, and a tomographic projection image 307 to which the elasticity is added is generated and displayed.

Next, the processing procedure of the volume rendering unit 17 for generating an ultrasonic projection image 300 in FIG. 3(c) will be described referring to FIG. 2. First, in step 201, the cutting plane 304 is set. This cutting plane 304 can be set at an arbitrary position or angle via the operation unit 4, with respect to the tomographic projection image 301 displayed on the display device 11. Here, in the volume rendering unit 17, the back side region (the opposite side of the viewpoint side) of the cutting plane 304 is set as a display area of the tomographic projection image by normal volume rendering. Therefore, the viewpoint-side region of the cutting plane 304 is set as a non-display region in which the tomographic projection image by normal rendering is not to be displayed, but is set to display a tomographic projection image having the property to be described later.

Next, volume rendering is to be started in step 202. Here, for explanatory reasons, the projection image to be displayed on a display region is set as the tomographic projection image by normal volume rendering, and the tomographic projection image to be displayed on a non-display region is set as the tomographic projection image having an elastic property on which the volume rendering process of the present invention is to be performed. First, the position of the processing target pixels on a projection plane are updated (initialized at first) in step 203, and the positions of the processing target voxels for rendering in the depth on a line of sight are sequentially updated (initialized at first) toward the depth side in step 204.

Next, on the basis of the projection plane, the coordinate positions of the updated processing target voxels are acquired (step 205), and whether or not the processing target voxels are within the display region is determined (step 206). If the voxels are in the display region, the luminance values of the processing target voxels are rendered, i.e. accumulated in step 208. On the other hand, when the processing target voxels are not within the display region, the elasticity value of the voxels in the elasticity volume data corresponding to the coordinate positions of the processing target voxels are read out, and whether or not the readout elasticity values satisfy a predefined threshold value or not in step 207. Here, a threshold value can be set in the condition that it should satisfy a certain value, or should satisfy the range having the lower limit value and upper limit value. When it is determined by step 207 that the elasticity values of the processing target voxels satisfy the threshold value, the luminance values of the processing target voxels are rendered in step 208.

On the other hand, when it is determined by step 207 that the elasticity values of the processing target voxels do not satisfy the threshold value and the rendering process in step 208 is completed, whether or not the rendering calculation up to the last voxel in the depth has been completed is determined in 209 with respect to the currently processed voxels on the line of sight. When it is determined by step 209 that the rendering calculation up to the last voxel in the depth direction is not completed, the step is returned to step 204 to update the positions of the processing target voxels and steps 205~step 209 are repeated.

When it is determined by step 209 that the rendering calculation has been completed up to the last voxel in the depth direction, whether or not the rendering process is completed in all pixels of the projection plane is determined in step 210. When if is determined by step 210 that the rendering calculation is not completed in all pixels of the projection plane, the step is returned to step 203 to update the positions of the processing target pixels, and steps 204~210 are repeated. When if is determined by step 210 that the rendering calculation is completed in all pixels of the projection plane, RGB conversion is performed in step 211 on the pixels of the tomographic projection image generated by rendering in accordance with the pixel value to apply predetermined coloring, and the process is completed.

Here, the processing of steps 203~210 will be further described in concrete terms. When processing target voxels on the line of sight corresponding to the processing target pixels on the projection image is in a display region, a 3-dimensional projection image can be obtained by calculating output pixel value $C_{out}$ of the processing target pixel by accumulating voxel value Ci, opacity Ai and gradient Si using the equations (1) and (2). The equations (1) and (2) are the volume rendering method which is commonly known as Levoy, etc.

$$C_{out} = C_{out-1} + (1 - A_{out-1}) \cdot A_i \cdot C_i \cdot S_i \quad (1)$$

$$A_{out} = A_{out-1} + (1 - A_{out-1}) \cdot A_i \quad (2)$$

Here, $C_i$ is the voxel value of the i-th voxel on the line of sight which is viewing a 3-dimensional image from a certain point on a created 2-dimensional projection plane, and when the data of N voxels is aligned on the line of sight, value $C_{out}$ becomes the final output pixel value in which the voxel values (i=0~N) are accumulated. $C_{out-1}$ is the accumulated value up to an (i-1)-th voxel.

Also, $A_i$ is the opacity of the i-th voxel exists on the line of light which takes values ranging from 0 to 1.0. $S_i$ is a weight component for shading and is calculated from the slope of luminance value $C_i$ which is the voxel value. For example, when the normal line to the plane centered on the i-th voxel matches the light source, the light is reflected most strongly and thus 1.0 is provided as $S_i$. When the light source is orthogonal to the normal line, 0.0 is provided as $S_i$. A highlighting effect is achieved accordingly. The initial values of Cout(i) and Aout(i) are zero, and Aout(i) is accumulated each time the voxel is passed, and is converged to 1.0 as shown in the equation (2). Thus, when the accumulated value $A_{out-1}$ of the opacities up to the (i−1)-th voxel is approximately 1.0 as shown in the expression (1), voxel value $C_i$ of the i-th voxel is not reflected in the image to be output. In this manner, when the i-th voxel on the line of sight is updated and reached the N-th voxel or when accumulated value $A_{out}$ of the opacity becomes approximately 1.0, the volume rendering on the line of sight is completed, and the line of sight is updated to the next pixel position.

Accordingly, in the volume rendering unit 17 of the present example, a 3-dimensional projection image of a tomographic image is generated based on the tomographic image volume data and elasticity image volume data, and transferred to the synthesis processing unit 10. By doing so, a tomographic projection image 307 shown in FIG. 3(c) on which the elasticity value is reflected is displayed on the display device 11, thus an examiner can observe the form of the tumor area 302 and the surrounding tissue shown in the tomographic projection image and make an accurate diagnosis. In other words, relation of the properties in the respective ultrasonic projection images that form the tomographic projection image 307 can be visualized for diagnosis, which broadens the potential of diagnosis.

In step 208, it also is possible to convert the voxel values of a tomographic image into color codes of RGB in accordance with a color scale and perform the integral processing for each element of R, G and B on the basis of the equation (1). In this case, it is not necessary to perform RGB conversion by step 211.

As described above, the present example comprises the volume rendering unit 17 configured to generate a tomographic projection image and an elasticity projection image by volume rendering the tomographic image volume data and elasticity image volume data of ultrasonic waves, and the display device 11 configured to display the tomographic projection image and the elasticity projection image generated by the volume rendering unit 17, wherein the volume rendering unit 17, for one of the rendering spaces partitioned by a cutting plane, renders the voxels of the tomographic image volume data corresponding to the voxels of the elasticity volume data having the elasticity values which satisfy a set threshold value so as to generate and display a tomographic projection image on the display device 11. That is, tomographic image volume data and elasticity image volume data of ultrasonic waves are obtained and the voxels of the tomographic volume data corresponding to the voxels of the elasticity image volume data having the elasticity values which satisfy a set threshold value are rendered in one of the rendering spaces partitioned by a cutting plane which is set in the rendering space, so as to generate and display a tomographic projection image on the display device 11.

The present example also comprises a memory unit (not shown in the diagram) configured to store tomographic image volume data and elasticity image volume data, and the operation unit 4 for setting a cutting plane to be set in a rendering space. The volume rendering unit 17, with respect to the other one of the rendering spaces partitioned by a cutting plane, generates a tomographic projection plane by normal rendering and displays the image on the display unit 11.

Accordingly, the region in which the tomographic projection image by normal volume rendering is to be displayed and the region in which the tomographic projection image by the volume rendering which is the characteristic of the present example are partitioned by the cutting plane 304, and the tomographic volume data of a tumor area which satisfies a threshold value is volume rendered, so as to generate and display a tomographic projection image thereof on the display unit 11. In this manner, even in a tumor area hidden by the surrounding tissue in the conventional technique, a tomographic image thereof can be generated and displayed by volume rendering the voxels having a certain range of elasticity values from among the voxels in the tomographic projection image referring to the elasticity values in the elasticity volume data. As a result, as shown in FIG. 3(*c*), only a part of the tomographic projection image 307 including the tumor area having a steric surface corresponding to the tumor area 302 from which the surrounding tissue is eliminated can be displayed in the region on the viewpoint side of the cutting plane. In other words, in a case of depicting a tumor having a specified hardness contained in the surrounding tissue with high luminance, in accordance with the present example, for example the tumor area 302, the cross-section 305 of the surrounding tissue and the tomographic projection image can be identified at the same time.

Example 2

Figure 4:
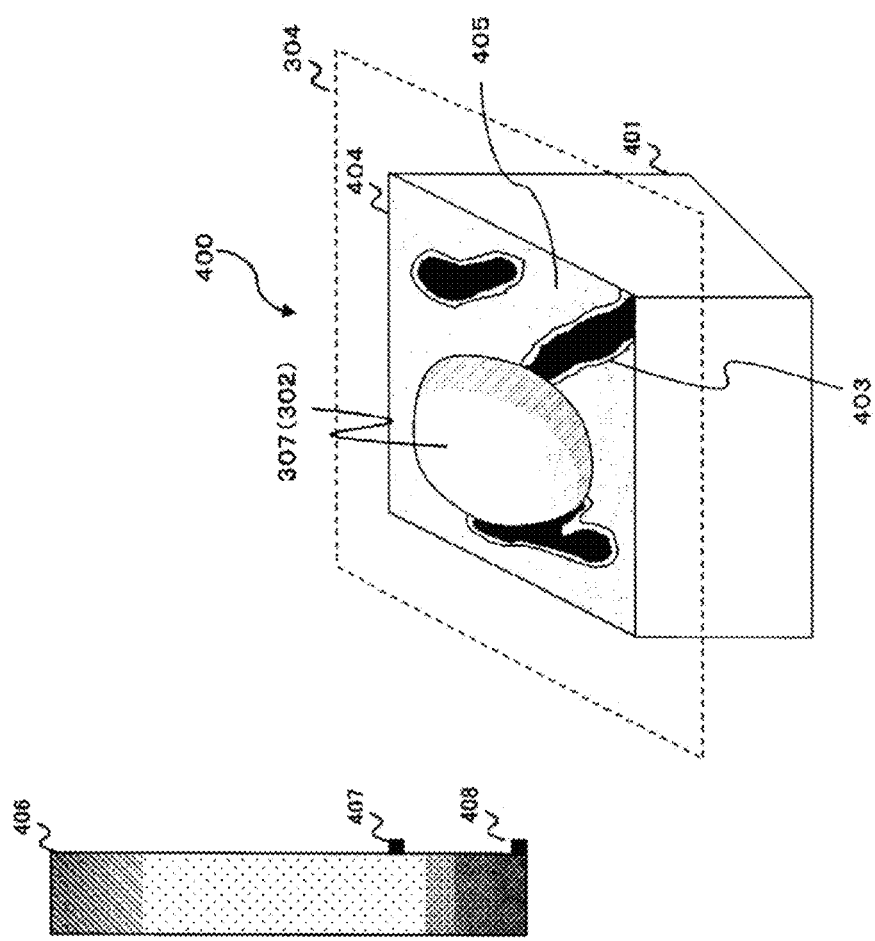
FIG. 4 is a display example of a tomographic projection image by Embodiment 2.

FIG. 4 is an example of an ultrasonic projection image 400 to be displayed by the present example 2. The volume rendering unit 17 of the present example is a modification of the volume rendering unit 17 in Embodiment 1, in which a cut cross-section 404 itself which is cut by the cutting plane 304 is set in the region in which a tomographic projection image by normal rendering is not to be displayed in addition to the display in the front side of the cutting plane 304, as shown in the diagram. Then a 2-dimensional tomographic cross-sectional image 405 in the cut cross-section 404 of the tomographic projection image 401 is displayed on the cut cross-section 404. The volume rendering unit 17 generates a tomographic cross-sectional image or elasticity cross-sectional image on the cutting plane 304 on the basis of the tomographic image volume data or elasticity image volume data, and makes the generated image displayed on the display device 11. A blood vessel image 403 is depicted on the displayed tomographic cross-sectional image 405. Also, the tomographic projection image 307 including the hard tumor area 302 is sterically displayed within the region of the tomographic cross-sectional image 405. By observing such ultrasonic projection image 400, the examiner can intuitively understand that a feeding blood vessel is flowing into the tumor area 302.

In FIG. 4, a color scale 406 of elasticity values is displayed with the ultrasonic projection image 400. The elasticity values are segmented into plural gradations in the color scale 406, and hues are changed in accordance with the gradation. Threshold marks 407 and 408 given to the color scale 406 indicate the range (the lower limit and upper limit) of the threshold value for the elasticity values to be displayed. The examiner can specify a region having the elasticity values to be displayed on the tomographic projection image 307, such as the hardness equivalent to a tumor, by variably setting the range of the threshold value via the operation unit 4. In this manner, the voxels having the elasticity values in the range of the threshold value set by the threshold marks 407 and 408 given to the color scale 406 are rendered, and the tomographic projection image 307 including the tumor area 302 is displayed. In other words, while the threshold marks 407 and 408 indicate a hard region, the 3-dimensional tomographic projection image 401 excludes only the soft region in the space region on the front side of the cutting plane 304.

Example 3

Figure 5:
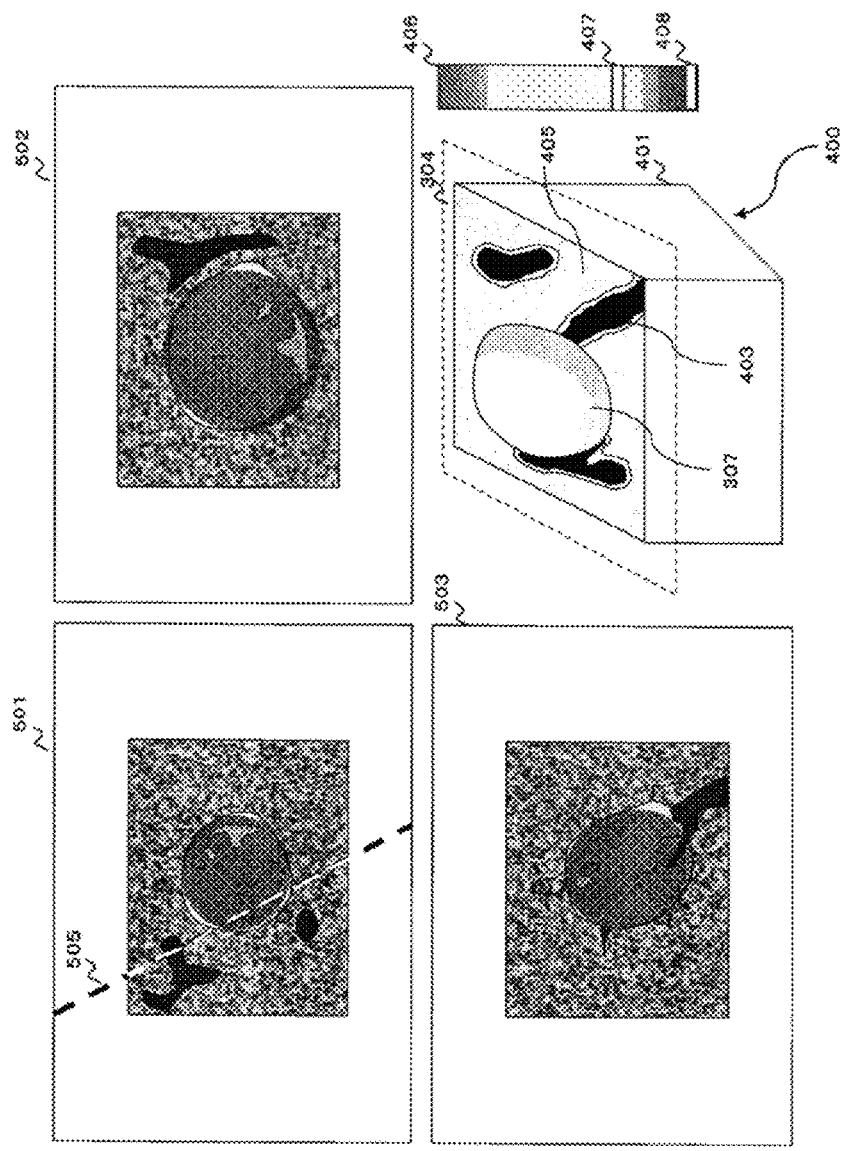
FIG. 5 is a setting example of a tomographic projection image, orthogonal 3-cross-sectional image and a cutting plane by Embodiment 2.

FIG. 5 shows an example of the ultrasonic projection image 400 to be displayed by the present Example 3. The present example displays arbitrary orthogonal 3-cross-sectional images of FIG. 1 created by the tomographic cross-sectional image creating unit 21 and the elasticity cross-sectional image creating unit 22 on the display device 11 with the ultrasonic projection image 400 of Embodiment 2. That is, a sagittal cross-sectional image 501, coronal cross-sectional image 502 and horizontal cross-sectional image 503 of the orthogonal three cross-sections are the images in which a tomogrpahic cross-sectional image and elasticity cross-sectional image created respectively by the tomographic cross-sectional image creating unit 21 and the elasticity cross-sectional image creating unit 22 are superimposed and displayed.

In the sagittal cross-sectional image 501 displayed on the display unit 11 in the present example, the cutting plane 304 can be set by setting a cut cross-section 504 via the operation unit 4. When the cutting plane 304 is set by the cut cross-section 505, it is set as the plane which is horizontally extended in the depth direction on the line of sight in a 3-dimensional volume, and the tomographic cross-sectional image 405 is created in accordance with the set plane on a 3-dimensional tomographic projection image. In this case, the cutting plane can be set referring to the tumor area in the sagittal cross-sectional image 501, thus the tumor area can be easily extracted. Also, by setting the threshold marks 407 and 408 of elasticity while referring to the color scale of the elasticity cross-sectional image which is superimposed on the sagittal cross-sectional image 501 of the tomographic image, the depicting range can be determined more intuitively.

Example 4

Figure 6:
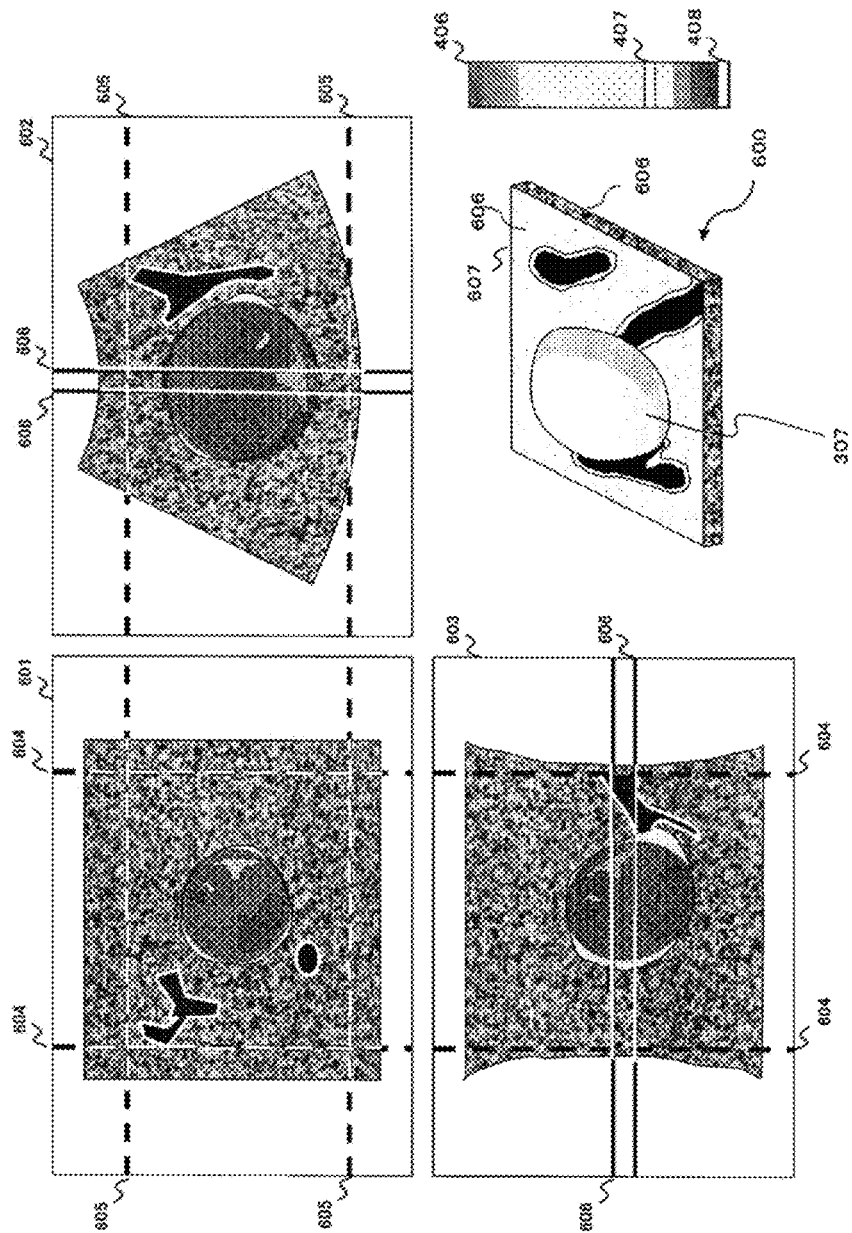
FIG. 6 is another setting example of a tomographic projection image, orthogonal 3-cross-sectional image and a cutting plane by Embodiment 4.

FIG. 6 shows an example of an ultrasonic projection unit 600 to be displayed by the present Example 4. The present example is a modification of arbitrary cross-sectional images of Embodiment 3 shown in FIG. 5, and another example of a cutting plane. That is an example that arbitrary orthogonal 3-cross-sectional images created by the tomographic cross-sectional image creating unit 21 and the elasticity cross-sectional image creating unit 22 shown in FIG. 1 are displayed with an ultrasonic projection image 600 on the display device 11. A sagittal cross-sectional image 601, coronal cross-sectional image 602 and horizontal cross-sectional image 603 of orthogonal three cross-sections are the images in which a tomographic cross-sectional image and elasticity cross-sectional image created respectively by the tomographic cross-sectional image creating unit 21 and the elasticity cross-sectional image creating unit 22 are superimposed and displayed.

In the present example, pairs of cutting planes 604, 605 and 606 are set which are parallel to the respective axes on the orthogonal three cross-sections. The pair of cutting planes may not always have to be parallel. The present example can cut out a 3-dimensional tomographic projection image 607 as a cuboid to depict the ultrasonic projection image 600. Here, even in a case that a tumor area is in the region in which the tomographic projection image by normal volume rendering is not displayed by the cut cross-section 606, the tomographic projection image 307 including the tumor area is sterically depicted by the threshold value range of the elasticity values set by the threshold marks 407 and 408 on the color scale 406, whereby enabling the display by which an examiner can easily identify the relationship between the tumor and the surrounding tissue.

Example 5

Figure 7:
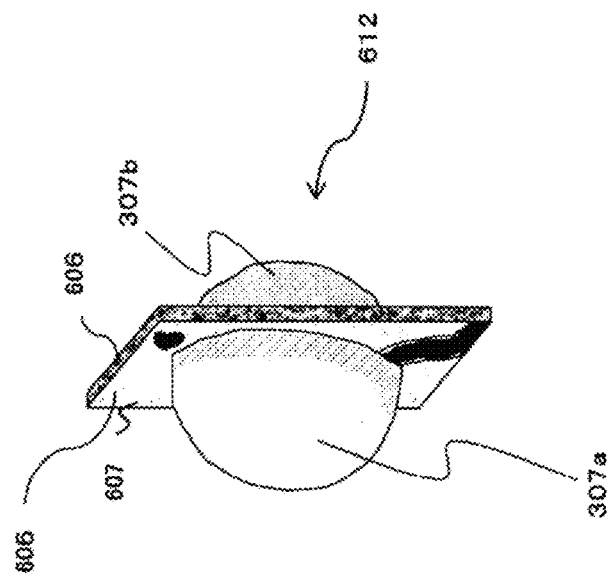
FIG. 7 is a display example of a tomographic projection image in Embodiment 5.

FIG. 7 shows a display example of an ultrasonic projection image 612 which is a modification of Example 4. The present example sets the outside of a pair of parallel cutting planes as the region in which a tomographic projection image by normal rendering is not displayed. In accordance with the present example, a tomographic projection image 307a of the upper side and a tomographic projection image 307b of the under side of the cut cross-section 606 in the tomographic projection image 307 including the hemispherical tumor area 302 are displayed. Further, the viewpoint of the ultrasonic projection image 612 can be freely rotated via the operation unit 4. This enables the examiner to intuitively identify 3-dimensional positional relationship among the tomographic projection images 307a and 307b that are on the upper side and the under side of the pair of parallel cutting planes and the cutting plane.

Example 6

Figure 8:
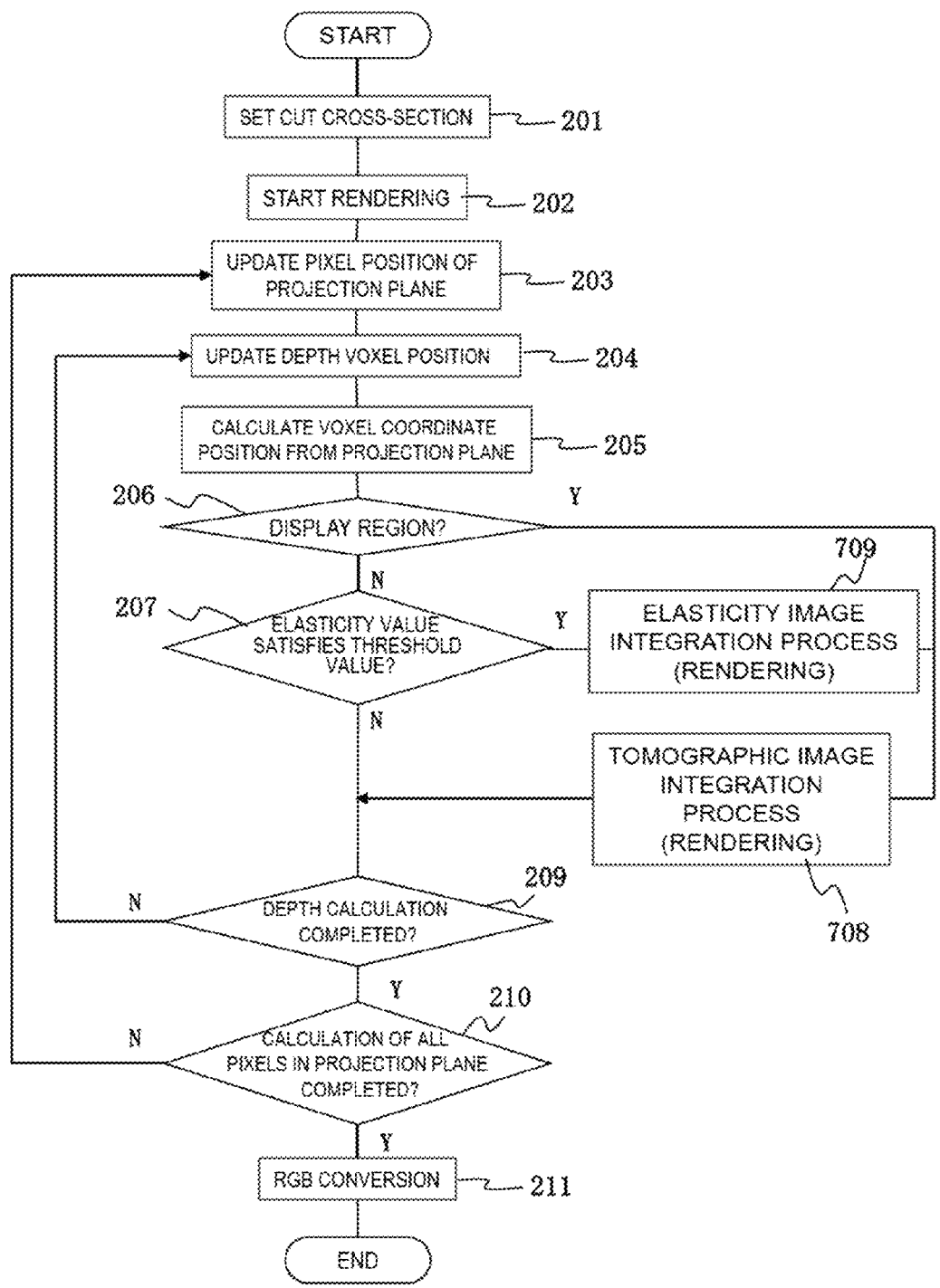
FIG. 8 is a flowchart showing the processing procedure of the volume rendering unit in Embodiment 6.

Example 6 of the present invention will be described referring to FIG. 8 and FIG. 9. The difference of the present example from Example 1, etc. is the rendering process to be performed in the volume rendering unit 17 of the ultrasonic diagnostic apparatus shown in FIG. 1. That is, the rendering process to be performed in the volume rendering unit 17 divides the integral processing (rendering) of step 208 in FIG. 2 into a tomographic image integral processing (rendering) 708 and an elasticity image integral processing (rendering) 709 as shown in FIG. 8. Rest of the procedure is the same as the operation flow shown in FIG. 2, thus the description thereof will be omitted.

In step 206, if processing target voxels are within a display region, integral processing of a tomographic image is performed in the tomographic image integral processing (rendering) 708 according to the equations (1) and (2). When the target voxels are in the region on the viewpoint side of the cutting plane, whether or not the elasticity values in the processing target voxels satisfy the threshold value is determined in step 207. If the determination result of step 207 is positive, the integral processing is to be performed also on the elasticity image in the elasticity image integral processing (rendering) 709 according to the equations (1) and (2).

In other words, the integral processing is to be performed on the tomographic image volume data having the voxels with the elasticity values to be displayed whether or not the voxels are in the display region of a tomographic projection image by normal volume rendering.

On the other hand, only when the voxels are in the display region of the tomographic projection image and the elasticity values of the voxels do not satisfy the values to be displayed, the integral processing is not to be performed. Further, when the voxels are in the display region of the tomographic projection image and the voxels have the elasticity values to be displayed, the integral processing of the elasticity image is to be performed.

In the volume rendering unit 17 of the present example, as described above, a 3-dimensional tomographic projection image is generated in which an elasticity projection image is superimposed thereon based on the elasticity image volume data and tomographic image volume data, then the generated image is transferred to the display device 11 via the synthesis processing unit 10. As a result, in accordance with the present example, it is possible to obtain a tomographic projection image in which only a tumor area on the viewpoint side of a cutting plane is colored by a color scale.

Also, the integral processing can be performed by each element of R, G and B on the basis of the equation (1), by converting the voxel values of the tomographic projection image and elasticity projection image into color codes of RGB according to the color scale in steps 708 and 709. In this case, only addition of the elasticity image and tomographic image needs to be performed without executing RGB conversion by step 211.

Figure 9:
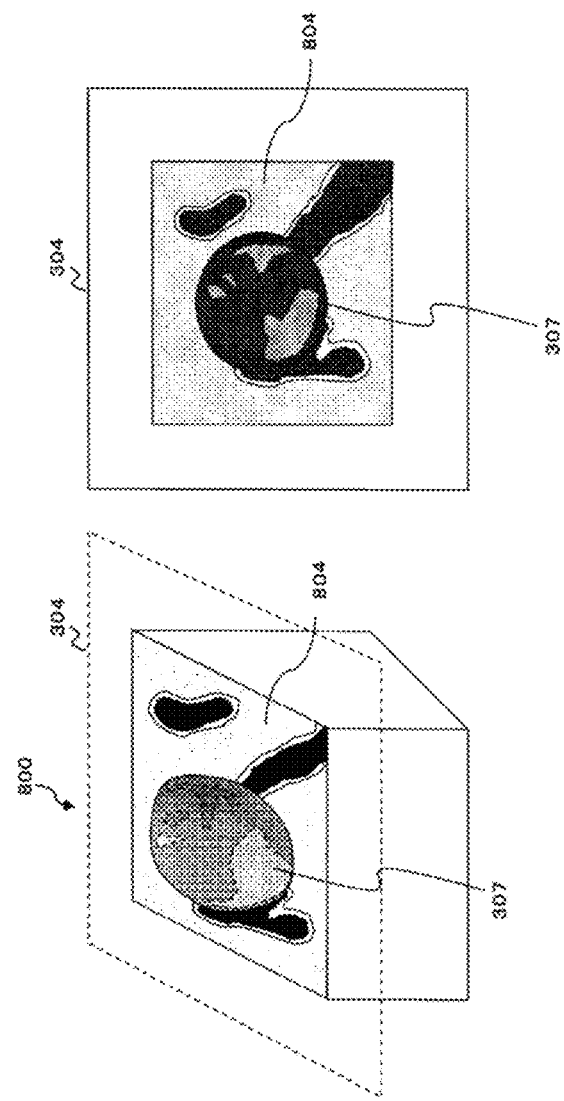
FIG. 9 is a display example of a tomographic projection image and an arbitrary cross-sectional image by Embodiment 6.

FIG. 9 is an example of an ultrasonic projection image 800 to be generated by the present example. As shown in the diagram, the tomographic projection image 307 of the tumor area 302 which is in the region on the viewpoint side of the cutting plane 304 is the image in which the elasticity projection image is superimposed onto the tomographic projection image. Also, the elasticity projection image of the tomographic projection image 307 is colored using the color scale in accordance with the elasticity values, thus the hardness thereof can be intuitively recognized. Also, creating a tomographic cross-sectional image and elasticity cross-sectional image in the cutting plane 304 in the tomographic cross-sectional image creating unit 21 and elasticity cross-sectional image creating unit 22 and a synthetic image 804 in which the previously created images are synthesized in the synthesis processing unit 10, and displaying the created images with the ultrasonic projection image 800, the examiner can correctly understand the hardness in the cutting plane 304.

Embodiment 2

Figure 10:
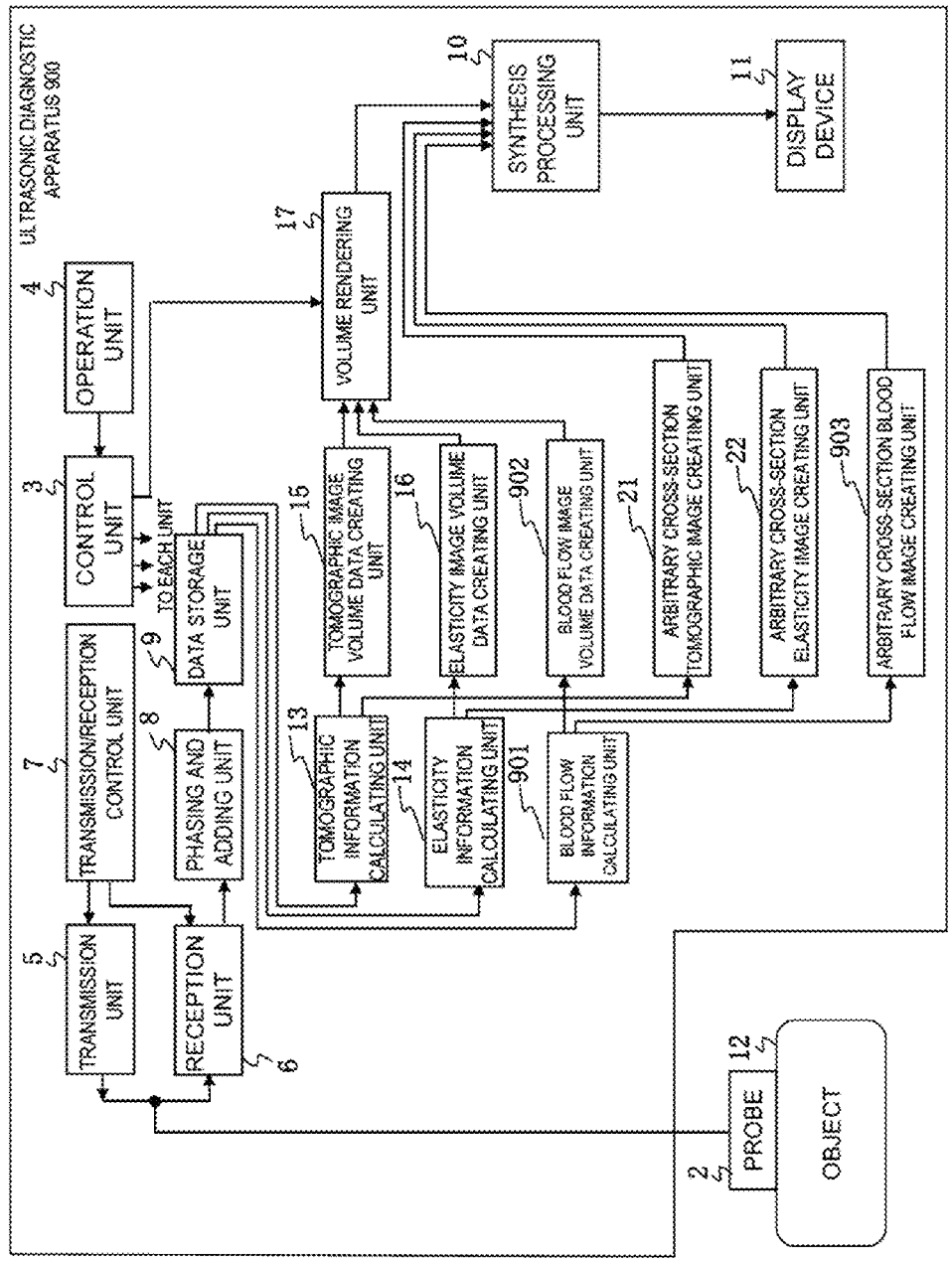
FIG. 10 is a block configuration diagram of an ultrasonic diagnostic apparatus in Embodiment 2 related to the present invention.

An ultrasonic diagnostic apparatus in Embodiment 2 to which the present invention is applied will be described referring to FIG. 10, FIG. 11 and FIG. 12. FIG. 10 is a block configuration diagram of an ultrasonic diagnostic apparatus 900 in the present embodiment. The difference between FIG. 10 and FIG. 1 is that a blood flow information calculating unit 901, blood flow image volume data creating unit 902 and a blood flow cross-sectional image creating unit 903 are provided.

The blood flow information calculating unit 901 calculates the blood flow information on the blood flow velocity or blood flow volume (power) using the frequency shift generated by Doppler from plural sets of RF signal frame data stored in the data storage unit 9. The blood flow image volume data creating unit 902 executes 3-dimensional coordinate conversion on plural 2-dimensional blood flow images on the basis of the transmission/reception directions ($\theta$, $\phi$) equivalent to the acquired positions of the 2-dimensional elasticity images, and generates the blood flow image volume data. To the blood flow image volume data, color values (for example, a color scale which changes from warm colors to cold colors depending on the direction) are provided according to the blood flow values. The memory unit can store the blood flow image volume data.

The blood flow cross-sectional image creating image 903 creates one or more 2-dimensional blood flow cross-sectional images relating to the orthogonal three cross-sections from the blood flow image volume data created in the blood flow information calculating unit 901, based on commands for specifying an arbitrary display cross-section set in the operation unit 4. The blood flow cross-sectional images created by the blood flow cross-sectional image creating unit 903 are transferred to the synthesis processing unit 10 with the respective cross-sections created in the tomographic cross-sectional image creating unit 21 and the elasticity cross-sectional image creating unit 22, and displayed on the display device, for example as superimposed images.

Figure 11:
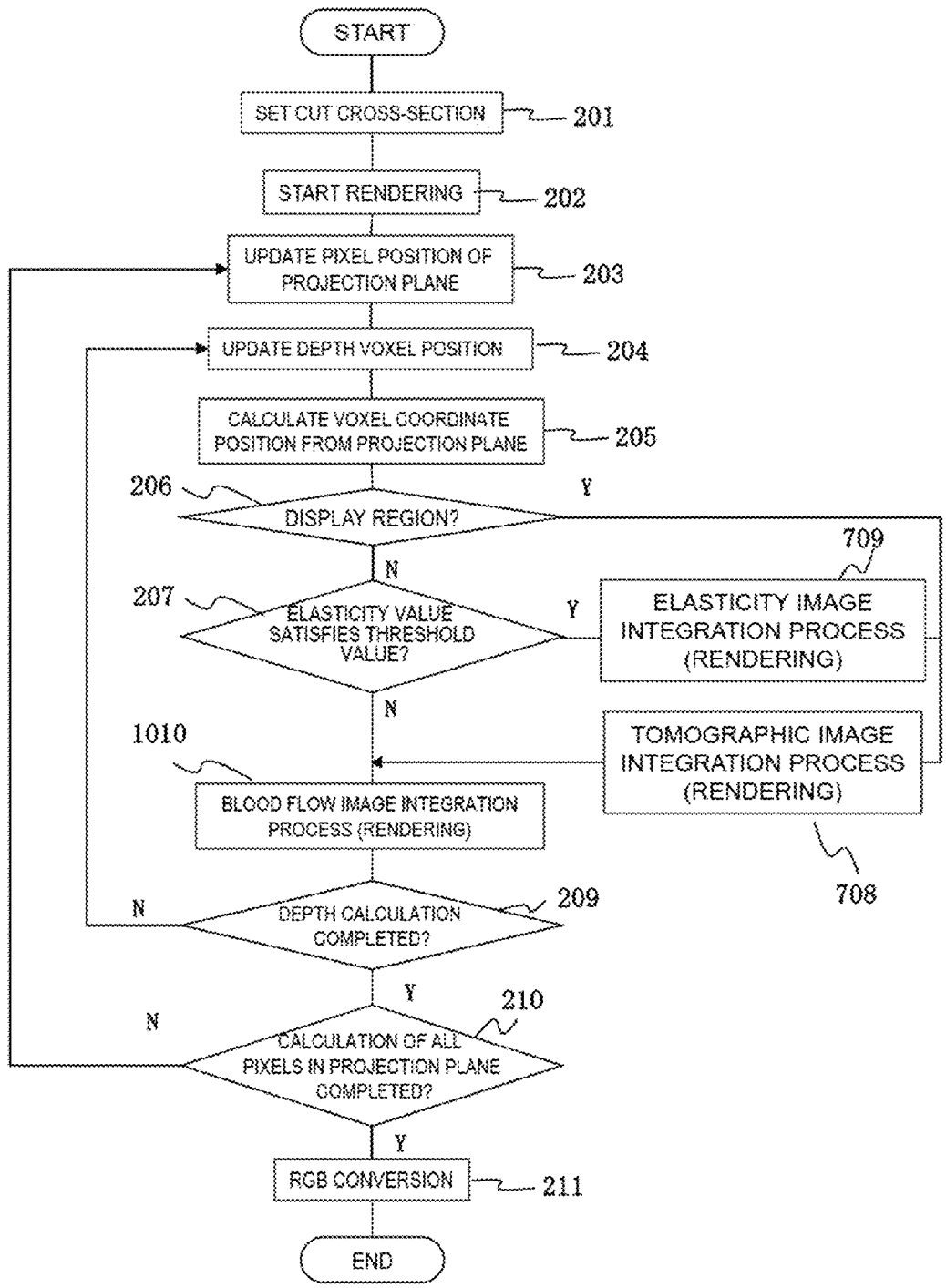
FIG. 11 is a flowchart showing the processing procedure of the volume rendering unit in Embodiment 2.

FIG. 11 is a flowchart of the rendering processing performed in the volume rendering unit 17 of the present embodiment. The difference between FIG. 11 and the flowchart in FIG. 8 is that step 1010 for performing blood flow image integral processing (rendering) is provided in the downstream side of step 207 or step 708. Rest of the flow is the same as in FIG. 8, thus the description thereof will be omitted.

Step 1010 for performing the blood flow image integral processing (rendering) executes the integral processing of the blood flow image volume data in the region on the viewpoint side of the cutting plane, regardless of whether or not the elasticity values satisfy the threshold value. As a result, the tomographic projection image of the region in the opposite side from the viewpoint side of the cutting plane is added to the tomographic projection image and blood flow projection image of the region on the viewpoint side of the cutting plane are added, and an ultrasonic projection image 1100 shown in FIG. 12(*a*) is created and displayed on the display device 11. As shown in the diagram, in the 3-dimensional ultrasonic projection image 1100, a tomographic projection image 1103 of the tumor area 302 which is in the region on the viewpoint side of the cutting plane 304 is colored, so that the hardness thereof can be intuitively recognized. Also, a 3-dimensional blood flow projection image 1105 is sterically displayed. As a result, by referring to the created projection images and a 2-dimensional cross-sectional image 1104 of the surrounding area at the same time, the examiner can easily understand the configuration of the area surrounding the tumor. In conclusion, in accordance with the present embodiment, 3-dimensional relationship between a tumor area and blood vessels can be easily recognized.

Also as shown in FIG. 12(*b*), by creating the tumor area 302 of a cross-section 1101 in the cutting plane 304, the blood flow image 403 and a tomographic image of the surrounding area in the tomographic cross-sectional image creating unit 21, the elasticity cross-sectional image creating unit 22 and the blood flow cross-sectional image creating unit 903 and displaying them as a synthetic cross-sectional image 1107, the examiner can correctly understand the hardness of the biological tissue in the respective areas at the position of the cutting plane 304.

DESCRIPTION OF REFERENCE NUMERALS

2 ultrasonic probe
3 control unit
4 operation unit
9 data storage unit
10 synthesis processing unit
11 display device
13 tomographic information calculating unit
14 elasticity information calculating unit
15 tomographic image volume data creating unit
16 elasticity image volume data creating unit
17 volume rendering unit
21 tomogrpahic cross-sectional image creating unit
22 elasticity cross-sectional image creating unit

The invention claimed is:

1. An ultrasonic diagnostic apparatus comprising:
a volume rendering unit, executed by a processor, that generates a tomographic projection image and an elasticity projection image by performing volume rendering based on tomographic image volume data and elasticity image volume data of ultrasonic waves; and
a display that displays a tomographic projection image and an elasticity projection image generated by the volume rendering unit,
wherein the volume rendering unit, for one of a plurality of rendering spaces partitioned by a cutting plane which is set in the rendering space, renders voxels in the tomographic image volume data, generates the tomographic projection image, and displays the tomographic projection image on the display,
wherein the volume rendering unit, for another one of the rendering spaces partitioned by the cutting plane set in the rendering space, renders the voxels in the tomographic image volume data corresponding to voxels in the elasticity image volume data having the elasticity values that belong to a set range, generates the tomographic projection image, and displays the tomographic projection image on the display.

2. The ultrasonic diagnostic apparatus according to claim 1,
wherein the volume rendering unit, with respect to the another one of the rendering spaces, further generates an elasticity projection image by rendering the voxels of the elasticity image volume data having the elasticity values that satisfy the threshold value and the tomographic projection image by rendering the voxels in the tomographic image volume data, superimposes the elasticity projection image on the tomographic projection image by rendering the voxels in the tomographic projection image, and makes the superimposed image displayed on the display.

3. The ultrasonic diagnostic apparatus according to claim 1, wherein the volume rendering unit, with respect to the region other than the tomographic projection image in the one of the rendering spaces, generates a blood flow projection image by volume rendering blood flow image volume data and displays the generated image on the display.

4. The ultrasonic diagnostic apparatus according to claim 1, wherein the volume rendering unit generates a tomographic cross-sectional image or an elasticity cross-sectional image on the cutting plane on the basis of the tomographic image volume data or the elasticity image volume data, and makes the generated image display on the display.

5. The ultrasonic diagnostic apparatus according to claim 3, wherein the volume rendering unit generates a blood vessel cross-sectional image on the cutting plane on the basis of the blood flow image volume data, and makes the generated image displayed on the display.

6. The ultrasonic diagnostic apparatus according to claim 1, wherein the volume rendering unit sets the cutting plane on one or more cross-sections of three orthogonal cross-sections to be displayed on the display using the tomographic image volume data.

7. The ultrasonic diagnostic apparatus according to claim 1, wherein:

the volume rendering unit sets the cutting plane as plural parallel cutting planes, and generates the tomographic projection image by rendering the voxels of the tomographic image volume data corresponding to the voxels of the elasticity image volume data having the elasticity values that satisfy the threshold value in the region outside of the plural parallel cutting planes.

8. The ultrasonic diagnostic apparatus according to claim 7, wherein the volume rendering unit sets the plural parallel cutting planes on the respective cross-sectional images of three orthogonal cross-sections to be displayed on the display.

9. The ultrasonic diagnostic apparatus according to claim 1, wherein the volume rendering unit applies colors on the tomographic projection image in accordance with the elasticity values, and outputs the colored image to the display.

10. The ultrasonic diagnostic apparatus according to claim 1, wherein the volume rendering unit variably sets a threshold value of the elasticity value within a range having an upper limit and a lower limit and displays an elasticity color scale with a tomographic projection image on the display, and the upper limit and the lower limit of the threshold value are displayed in an elasticity color scale.

11. The ultrasonic diagnostic apparatus according to claim 10, further comprising an operation unit, executed by a processor, to variably sets the upper limit and the lower limit of a threshold value of the elasticity value on the elasticity color scale displayed on the display.

12. The ultrasonic diagnostic apparatus according to claim 1, further comprising an operation unit, executed by a processor, that sets a cutting plane to be set in the rendering space.

13. The ultrasonic diagnostic apparatus according to claim 1, further comprising memory that stores the tomographic image volume data and the elasticity image volume data.

14. An ultrasonic image display method comprising:
obtaining tomographic image volume data and elasticity image volume data of ultrasonic waves;
generating a tomographic projection image by rendering voxels of the tomographic image volume data for one of a plurality of rendering spaces partitioned by a cutting plane which is set in the rendering space; and
displaying the generated tomographic projection image on a display, wherein, for another one of the plurality of rendering spaces partitioned by the cutting plane set in the rendering spaces, rendering the voxels in the tomographic image volume data corresponding to voxels in the elasticity image volume data having elasticity values that belong to a set range, generating the tomographic projection image and displaying the tomographic projection image on the display.

* * * * *